United States Patent
Orr, Jr.

[11] 3,943,754
[45] Mar. 16, 1976

[54] METHOD AND APPARATUS FOR DETERMINING THE RELATIVE WEIGHT PROPORTIONS OF DIFFERENT SIZE FRACTIONS OF A SAMPLE OF PARTICULATE MATERIAL

[75] Inventor: Clyde Orr, Jr., Atlanta, Ga.
[73] Assignee: Georgia Tech Research Institute, Atlanta, Ga.
[22] Filed: June 30, 1975
[21] Appl. No.: 591,407

[52] U.S. Cl. ............... 73/61.4; 73/432 PS; 209/237
[51] Int. Cl.² ............................................ G01N 15/02
[58] Field of Search ......... 73/61.4, 432 PS; 209/10, 209/237

[56] References Cited
UNITED STATES PATENTS

| | | | |
|---|---|---|---|
| 2,202,189 | 5/1940 | Cotton, Jr. et al. | 209/237 |
| 2,264,223 | 11/1941 | Stancliffe | 73/432 PS |
| 2,782,926 | 2/1957 | Saxe | 73/432 PS |
| 3,419,139 | 12/1968 | Agthe | 73/432 PS |

Primary Examiner—S. Clement Swisher
Attorney, Agent, or Firm—Newton, Hopkins & Ormsby

[57] ABSTRACT

A sample of particulate material is entrained in a moving body of fluid and the fluid is continuously discharged through a porous weighing member. Before passing to the weighing member sized fractions within the sample, except for the smallest one, are separated and held back at different regions in the body of fluid so that only the one fraction initially deposits on the weighing member. The weight addition of this fraction is measured and then a further fraction is re-entrained to move with the fluid to pass to and deposit on the weighing member cumulatively with the first fraction. The weight increase caused by this further deposition is measured and the re-entrainment and weight increase measurement of still further fractions are effected separately and successively until all fractions are deposited on the weighing member. These individual weights and their sum are recorded either manually or automatically and from them size percentages are computed. Further samples may be similarly processed while the weighing member accumulates all samples until its capacity is reached, whereafter the weighing member must be cleaned or replaced. The several size fractions may be separately recovered when a multiplicity of weighing members is employed.

10 Claims, 4 Drawing Figures

METHOD AND APPARATUS FOR DETERMINING THE RELATIVE WEIGHT PROPORTIONS OF DIFFERENT SIZE FRACTIONS OF A SAMPLE OF PARTICULATE MATERIAL

BACKGROUND OF THE INVENTION

Measurement of the size of particles in a particulate mass is required in a great many industrial operations. Specifically, the minerals industry needs to know when an ore has been sufficiently crushed. To build highways and large buildings, the soil must be analyzed for stability, one factor of which is particle size. Many products, notably pigments, have to be ground to required particle sizes.

Much of this particle sizing is now accomplished manually by having a technician expose samples of the powder to a series of sieves — pans with woven wire bottoms — from which, by weighing the amounts passing and retained, he can calculate percentages of particles having certain sizes. The work is tedious and time consuming. Many industrial materials are processed wet. This means that a sample has either to be dried before sieving or sieved and then the fractions dried in order to weigh them accurately.

Basically, sieving a powder to obtain its particle size distribution is quite simple when performed manually. It is a tedious and time consuming procedure, nevertheless. A series of sieves — usually pans with wire grid bottoms — are arranged vertically one above the other with the coarsest grid on top and the finest on the bottom. The powder in question is poured on the top sieve, and the sieves are shaken or vibrated until the particles distribute themselves in discrete fractions on the sieves. The fractions and the powder passing the finest sieve are weighed individually and the mass percentage retained (or passing) is calculated in terms of the sieve size openings.

The test may be performed with either a wet or a dry powder. In dry testing, complete dryness is required to eliminate moisture-formed aggregates, but frictional effects often give rise to electrostatic charges which cause the particles to adhere to one another and to the sieves, both retaining frame and wire grid. Some particles are usually lost by dusting also. Wet sieving requires repeated flushing with fresh water which means that if fractional sizes are to be determined, the portion of the powder passing all sieves must be captured by filtering or that the initial powder mass must have been determined, which usually means that another complete sample has to be evaporated to dryness. The fractions collected on each sieve must also be dried and then weighed in order for mass percentages to be calculated. Handling the finer sieves in either wet or dry sieving poses a problem because they are quite easily damaged.

Sieving has great industrial appeal as a means for size analysis despite its disadvantages because it gives a direct measurement, the basis for which is quite evident. In present practice, results are subject to considerable error because of losses due to handling, uncertainties of drying and weighing, incomplete separation, electrostatic effects (when dry), damaged sieves, and the like. Often only one fractionation, i.e., one separation into those particles larger and those smaller than a certain sieve size, is employed in control procedures in the interest of saving time and reducing manual effort.

Various mechanisms have been provided in order to improve upon the above purely manual technique. For example, a set of sieves each of a predetermined standard weight may be employed to avoid the necessity for transferring each fraction from its sieve to a weighing pan. Each sieve with its fraction is weighed directly (after drying, in the case of wet sieving). Various mechanical shakers have been provided for the sieves, including a type which shakes the sieves one at a time. This relieves the technician of the task of manually shaking the sieves.

Sieve separation as described above is practiced for reasons other than size measurement. Sometimes the reason is to learn through subsequent chemical analysis how composition changes with particle size. Such information is necessary in mineral recovery operations where the need is to determine how fine to grind for optimum mineral release. At other times it is to establish the most desirable particle size for a material in subsequent use, for example as a filler in a floor tile or cover. The present invention permits ready fractionation of powders into discrete size ranges for these purposes also.

BRIEF SUMMARY OF THE INVENTION

Basically, the present invention is directed to method and apparatus whereby different size fractions of a sample of particulate material are successively directed while entrained in a moving stream of fluid to a collecting station whereat each fraction is deposited in turn on a porous weighing member having interstices passing the fluid but not the sample fractions. On the way to the weighing station, the various fractions are formed within the conveying fluid and successive fractions are held back or retained until the preceding fraction has been deposited and its amount weighed. Actually the true weight is not obtained because buoyancy effects are neglected. Since the buoyancy correction is a constant, it does not alter the relative magnitudes of the measured weights, however. Each fraction is retained by the porous weighing member so that successive fractions accumulate in the weighing member. After one sample has been processed, a further sample may be processed without removing the first sample from within the weighing member by resetting the weighing member weight to zero.

The fluid is continuously moving and the apparatus involves a series of sieves of progressively smaller opening size downwardly through which the moving fluid and entrained material is passed. To aid in classifying the fractions on the sieves a pulsating backward and forward flow is superimposed upon the fluid as it passes through the sieves, thus periodically agitating all fractions. The smallest fraction or fines, not being retained by any sieve, is passed directly to the weighing station and when this entire fraction has been deposited and weighed the next larger fraction on the lowermost sieve is re-entrained by changing the course of fluid flow and it is then deposited to accumulate with the fines and the weight increase caused by this accumulation is then measured. This process is repeated until all fractions have been accumulated in the weighing member.

Re-entrainment of each fraction may be effected by selectively effecting a swirling action within an entrapment chamber, the swirling action being effected by tagential entry of the conveying fluid in one embodiment. In another embodiment, the re-entrainment is effected by selective energization of a paddle assembly which preferentially directs the material to a central fluid discharge point. The paddle in one embodiment is driven through a flexible tube outside but concentric with the discharge tube. This arrangement provides no horizontal and stationary surface onto which particles might settle and thus in no way degrades the size separation provided by this invention.

Structural features of one embodiment of the siever assembly include a stacked arrangement of components whereby ready assembly and disassembly is possible. In one embodiment this is accomplished without the need for connection and disconnection of fluid lines by constructing the sieve chamber walls with appropriately arranged parts. Pulsation of the conveying liquid within the siever assembly is effected by a pump which advantageously is in the form of either two sealed pistons in separate chambers or of one loose fitting, double acting piston within a single cylinder. The latter arrangement is generally preferred because it allows overall equalization of the pressure within the siever and thus avoids excessively high pressure peaks which might otherwise cause equipment damage.

It will be recognized that a multiplicity of weighing, or collecting members connected separately to individual sieve chambers would allow recovery of each particle size fraction. While the preceding description referred only to one weighing station, multiple collecting stations providing for discrete size fraction recovery are a part of this invention.

BRIEF DESCRIPTION OF THE DRAWING FIGURES

DETAILED DESCRIPTION OF THE INVENTION

Figure 1:
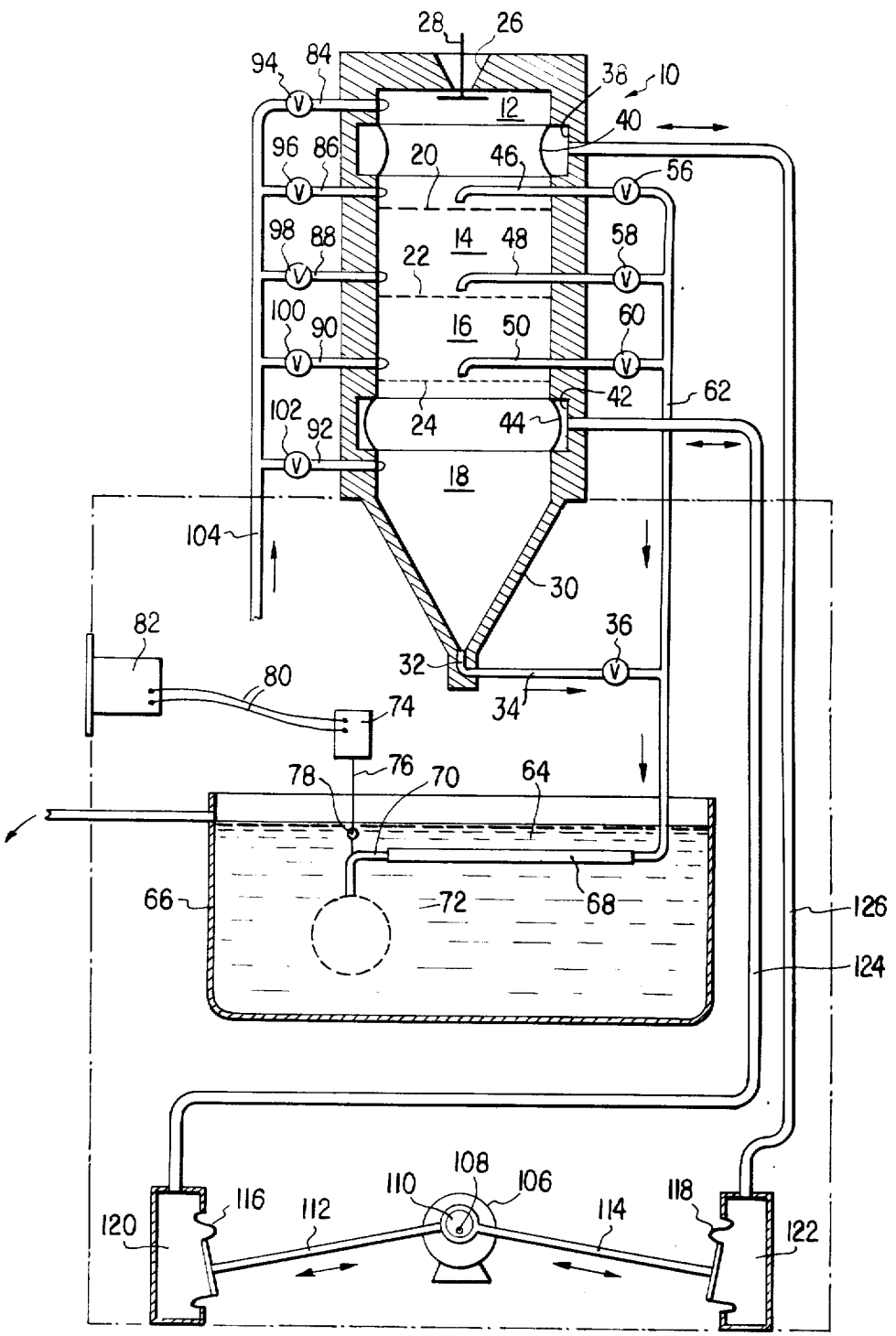
FIG. 1 is a vertical section taken through one embodiment of the invention.

Referring at this time more particularly to FIG. 1, the general principles of the present invention will be apparent therefrom. As shown, the method according to the present invention may be practiced in an apparatus generally as shown which includes a body indicated generally by the reference character 10 having a plurality of chambers 12, 14, 16 and 18 therein which chambers are separated by the sieves or screen members 20, 22 and 24. At the upper end of the body 10 there is provided an inlet opening 26 and an associated shut off valve 28 the purpose of which will be presently apparent and at the lower end of the body, and more especially at the apex of the inverted conical lower section 30 thereof there is provided a discharge passage 32 which communicates through the line 34 with a valve 36. At the upper end of the body, within the chamber 12 there is provided an annular recess 38 which is closed off by a band-like flexible and elastic membrane 40 and in the lowermost chamber 18 there is a similar annular recess 42 which is closed off by these flexible and elastic band-like membranes 44.

Figure 2:
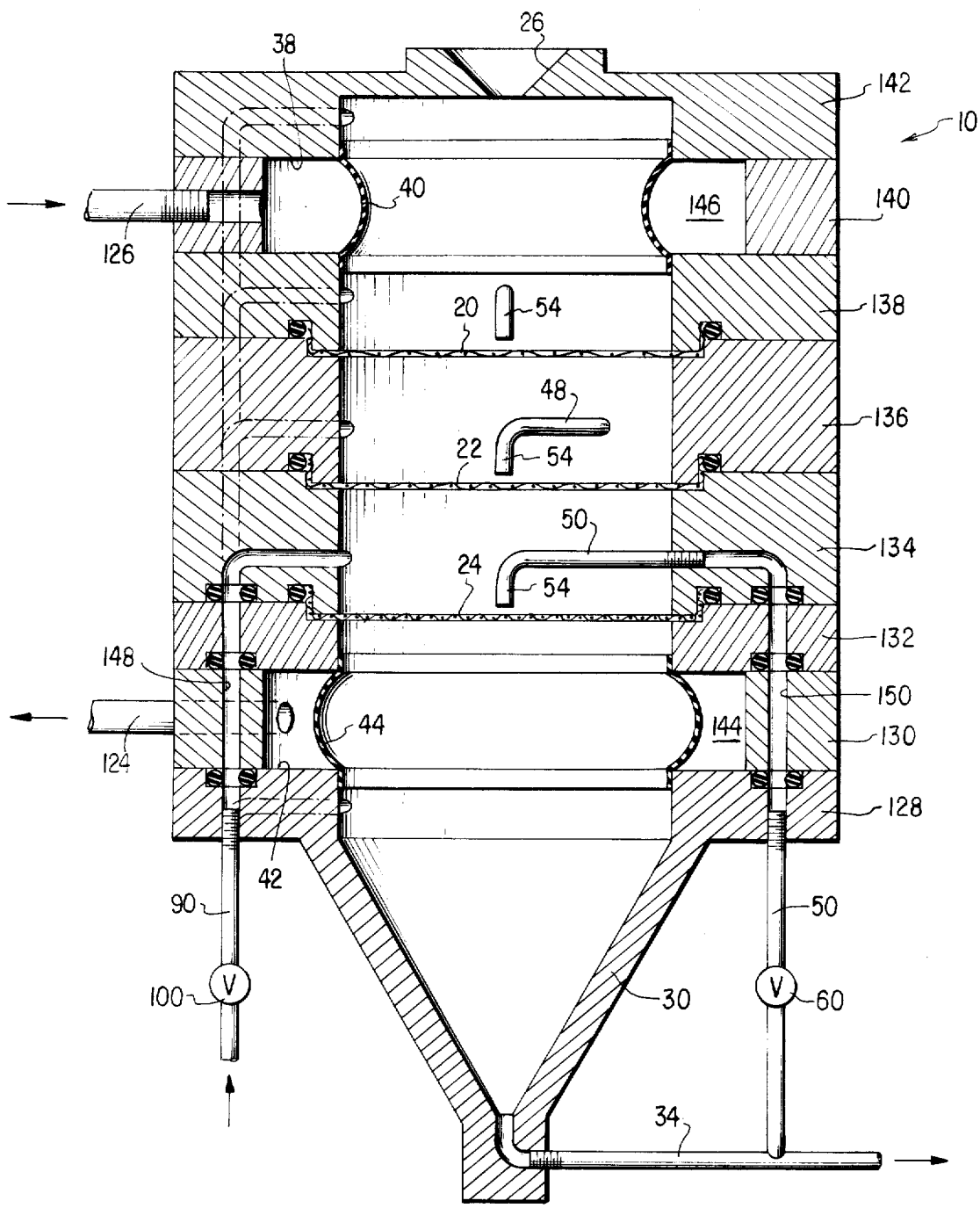
FIG. 2 is a more detailed vertical section taken through the embodiment of the invention in FIG. 1.

Associated with each of the screens, 20, 22 and 24 is a selective discharge pipe, same being indicated in FIG. 1 by the respective reference characters 46, 48 and 50, each of which pipes extends from a downturned inlet tip 54 as shown on FIG. 2 to a point exteriorally of the body 10 where it is connected to one of the valves indicated by the reference character 56, 58 and 60 to the common discharge line 62 to which the discharge pipe 34 is also connected through the valve 36. The discharge pipe 62 projects downwardly into a body of liquid 64 contained within a suitable tank 66 and is connected through a flexible member 68 to the L-shaped inlet tube 70 of a porous material-retaining member 72. Associated with the member 72 is a weighing device 74 which includes a mechanical transducer link 76 pivotally connected as at 78 to the pipe 70. The member 74 itself constitutes an electrical transducer element connected by suitable wires 80 to the read out device 82 which displays as for example by a swinging arm the weight of material contained within the porous pocket or material-retaining member 72. As will be presently apparent, it is advantageous to have the read out device 82 calibrated such that the tare weight imposed upon the transducer 74 through the mechanical link 76 due to the weight of the member 72, 70 and effect of the flexible member 68 is compensated for so that the read out is 0 when the member 72 is empty of material.

Associated with several chambers 12, 14, 16 and 18 are the liquid inlet lines indicated by the reference characters 84, 86, 88, 90 and 92 each of which inlet pipes leads into the chamber with which it is connected to discharge tangentially around the inner wall surface thereof, the purpose of which will be presently apparent. Each of these liquid inlet lines has associated with it a valve which are respectively identified by reference characters 94, 96, 98, 100 and 102 all leading to a common inlet line 104.

To complete the structural assembly as shown in FIG. 1, there is provided a suitable drive device such as the electric motor 106 having an output shaft 108 provided with an eccentric 110, there being two connecting rods 112 and 114 associated with this eccentric 110 correspondingly to operate the flexible membranes 116 and 118 of the two pump chambers 120 and 122. The pump chamber 120 is connected through a line 124 to the annular space behind the elastic membrane 40 and the other pump chamber 122 is connected through the line 126 to the space behind the elastic membrane 44. From the connection as shown, it will be apparent that as one membrane 40 is being stretched to expand radially inwardly, the other membrane 44 is being stretched outwardly, as shown and vice versa.

To utilize the assembly as is illustrated in FIG. 1, a sample of mass of particulate material having particles of varying sizes is charged into the uppermost chamber 12 through the opening 26 whereafter the valve 28 is closed to prevent escape of liquid therefrom. The body 10 is filled with water or other conveying liquid through the inlet 104, the purpose of which initially all of the valves 94, 96, 18, 100 and 102 may be open, the body 10 being filled before the introduction of the charge of particulate material thereinto. When the particulate material is charged into the body 10 and specifically into the uppermost chamber 12 thereof, the valves 96, 98 and 100 are closed whereas the valves 94 and 102 are open and at this time also the several valves 56, 58 and 60 are closed and the valve 36 is open. Valve 94 is open to create a downward flow of liquid in body 10 and valve 102 to create a swirling flow in the conical region 30 and thus to prevent deposition of fines. At the same time, the motor 106 is operated to cause a pulsating action of the liquid within the body 10 back and forth across the several screens or sieves 20, 22 and 24 which separate the chambers as aforesaid. Thus, there is a net flow of liquid through the pipe 104 and valve 94 into the uppermost chamber. The pulsating action within body 10 and the generally downward flow of liquid through it causes excellent classification of the various particle sizes onto the several screens 20, 22 and 24, the screen 20 having the largest openings, the screen 22 having the next smaller openings and the screen 24 having the smallest openings. Some of the material which is of the smallest particle size such as to pass the screen 24 passes into the lower chamber 18 and ultimately is discharged through the outlet 34, the valve 36 and into the discharge pipe 62 through the flexible line 68 and into the interior of the material-retaining member 72 wherein it is trapped. As noted previously, the member 72 is porous so that the liquid can pass freely therethrough but the particulate material is retained therewithin. The read out device 82 indicates the accumulation of fines. When the accumulation substantially ceases as indicated by the constancy of the read out device all of the fines will have passed into and be retained within the member 72. It should be noted that in operation of the device, the initial condition may be such that both valves 94 and 102 are open or any combination may be effected in the operation therebetween such as assures initially the proper classifying action and the necessary scouring action of the lowermost chamber 18.

At this point, the net relative weight of the material which is the fines retained within the 72 is recorded. It may be noted that for most accurate reading at this point, any flow of liquid can be terminated as by closing all of the valves 94 and 102 and 36 which may previously have been opened but this is not necessary since the flow out of member 72 is effectively equal in all directions and thus influences the weighing only insignificantly. As soon as this reading is taken, the valves 102 and 36 are closed and valves 100 and 60 are opened which allows some of the conveying liquid to be discharged tangentially through the inlet 90 into the chamber 16 to cause a swirling action therein tending to migrate all of the retained particulate material towards the center whereat the tip 50 of the pipe is indicated so as to pick up all of the retained particulate material in the chamber 16 ultimately to discharge it through the valve 60 and the line 62 into the interior of the member 72. During this action, the pulsating action as effected by the motor 106 is of course effected positively to assure that no particulate material is retained on the screen 24 but is instead all discharged into the member 72. At this point, another reading is taken at the read out 82 and this reading is recorded subsequent of course to closure of the valves 100 and 60. Next, the valves 98 and 58 are opened and the process is repeated and, lastly the valves 96 and 56 are opened to batchwise discharge the largest particulate material particles into the material-retaining member 72.

It will be obvious, of course, that the relative weights of all of the fractions of various sizes of particulate material may be obtained in this way. Exact weights are not obtained since the buoyancy of the water is not taken into account. Relative weights, however, are sufficient for calculating the percentages of mass represented by the several fractions. Mass percentages are the information desired in particle size analysis. It should also be noted that quite a number of successive sample batches may be processed without cleaning out the contents of the member 72, simply either by recalibrating the read out device 82 or simply keeping a running record of the successively greater weights displayed thereat.

Defined at this time more particularly in FIG. 2, one form in which the body 10 may take is illustrated therein. Thus, as shown, a succession of stacked rings or plates 128, 130, 132, 134, 136, 138, 140 and 142 are shown, the lowermost of which includes the inverted conical section 30 as previously described. The two annular sections 130 and 140 define the pulsating chambers 144 and 146 with their associated membranes 44 and 40 and the respective screens or sieves 20, 22 and 24 are sandwiched between the corresponding pairs of sections 138, 136; 134, 136; or 134, 132. Through bolts or other suitable means not shown may be utilized to maintain the stack of plates or disc sections in tightly sealed relationship and the inlet conduits are formed by axially extending bores such as the bore 148 shown for the inlet section 90 and extending through the requisite number of plates or discs. The remaining inlets are staggered circumferentially around the device as is indicated by the phantom lines. Correspondingly, the outlet sections are formed by axially extending bores 150 as shown for the outlet section 50 and these two are circumferentially staggered around the device as will be apparent from FIG. 2.

Figure 3:
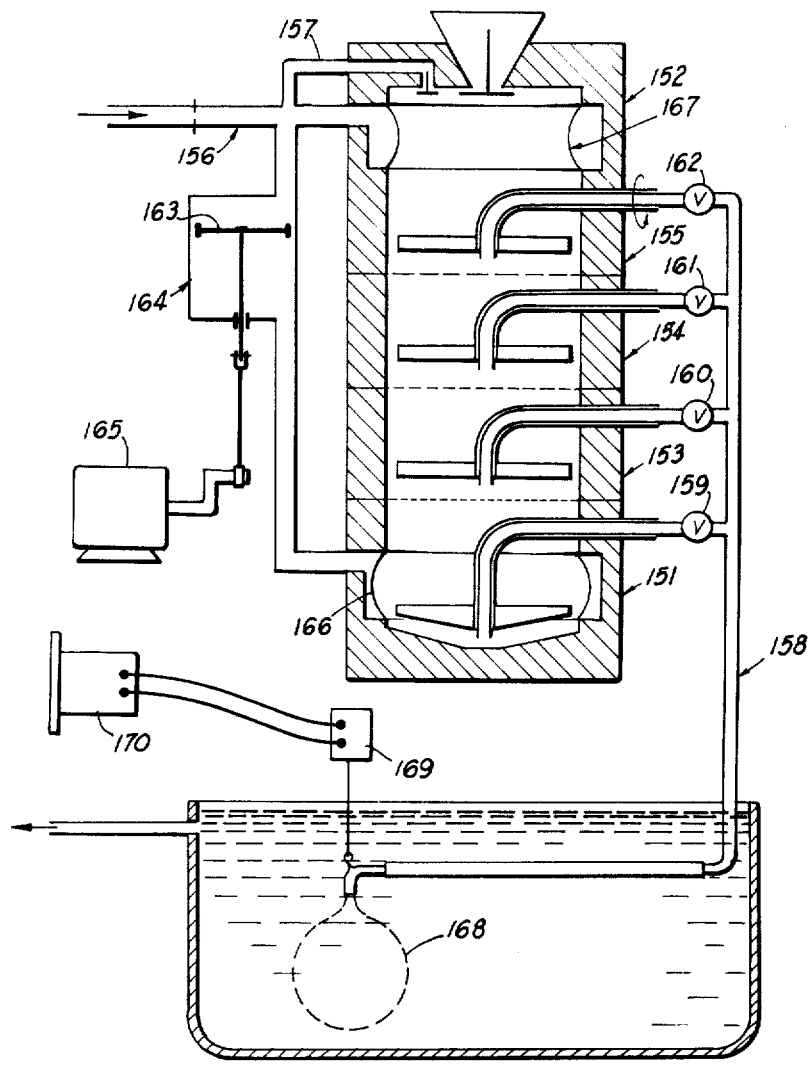
FIG. 3 is a vertical section showing another embodiment of the invention.

Alternatively, the embodiment may be formed as is shown in FIG. 3 wherein end sections 151 and 152 may be utilized in stacked configurations with sieve sections 153, 154 and 155 therebetween. Liquid enters through pipes 156 and 157 and, with entrained and fractionated particles, leaves through pipe 158 by way of one of the valves 159, 160, 161 or 162. Loose-fitting piston 163 moving up and down in cylinder 164 as driven by gear motor 165 produces a pulsating action in the liquid through the elastic membranes 166 and 167. As in the embodiment of FIG. 1, the particles are cumulatively collected in weighing member 168. Their relative weights are detected by transducer 169 and indicated on read out 170.

Figure 4:
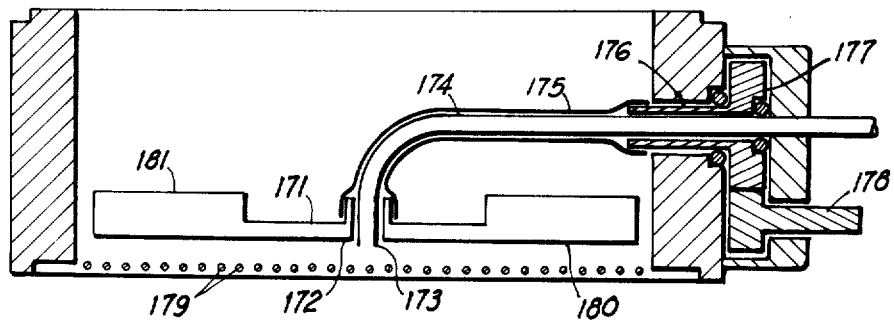
FIG. 4 is an enlargement of a portion of FIG. 3 showing greater detail.

FIG. 4 illustrates a further detailed embodiment of one sieve section such as 154 of FIG. 3 to require a smaller fluid flow rate as compared with previous embodiments and also being effective to assure that larger or denser particles are re-entrained efficiently.

In this form of the invention, the tangential inlet for fluid is eliminated and a paddle or blade assembly 171 causes the movement of particles to the center of effect removal.

The paddle assembly includes a hub 172, rotatably mounted on the downturned end 173 of the outlet pipe 174, which hub is connected by an elastic tube 175 to one end of a shaft 176 disposed around the pipe 174. The outer end of the shaft 176 is provided with a suitable gear drive and seal at 177, the gear meshing with another gear and shaft 178. Rotation of shaft and gear 178 causes gear and shaft 176 to rotate which in turn moves paddle 171. Obviously, shaft 178 may be rotated by means of a suitable motor.

Pipe 174 openly communicates with the outside thereby serving to define an outlet for re-entrained material which passes to an outlet valve, 161 of FIG. 3, under the conditions previously set forth. Because the paddle assembly 171 performs the re-entrainment and directing of the material to the inlet 173 in the hub 172, the flow rate through the outlet 174 need not be as great as, say, in FIG. 1.

The paddle assembly 171 is mounted above the sieve 179 and includes oppositely directed radial arms, each mounting a paddle blade 180 and 181. These blades are mounted at angles with respect to their respective arms, their angularity being such as to create a radially inward feeding motion to the particulate material which, by virtue of the pulsating fluid flow action, is repeatedly lifted off the sieve 179 ultimately to reach and pass through the inlet 173 with the fluid within which it will now be entrained.

While FIGS. 1, 2 and 3 each show three sieve sections it will be obvious that both greater and lesser numbers of sieves could be employed.

Likewise, FIGS. 1 and 3 each show one weighing member in which particles are collected. It will be obvious that a multiplicity of weighing or collecting members could be employed as long as collectively they are attached to a single weighing transducer. Referring to FIG. 1, outlets 34, 46, 48 and 50 could be directly attached through individual flexible members such as 68 to a collecting member such as 72.

Both FIGS. 1 and 2 show pulsating mechanisms driven directly by constant speed motors through fixed mechanical linkages. Obviously pulsation cycle speed could be changed by changing motor speed and pulsation magnitude by altering the cam throw. Both need to be adjustable to obtain maximum efficiency with particles of different size and density.

One of the major problems with all sieving devices is the hanging of particles of nearly screen opening size within the screens. Once so caught, they are difficult to dislodge. Pulsation that is of equal intensity both upward and downward neither alleviates nor increases this problem. One aspect of this invention not heretofore noted is provision for the upward pulse to be of greater intensity than the downward pulse. This is accomplished by driving the electric motor that produces the pulses in a cyclical manner by means of well-known electronic circuits and a timer. In this way the motor will be speeded when the liquid within the sieving sections is moved upward and slowed when the liquid is moved downward. Particles will thus fall on the sieve screens with less energy than that with which they are raised above the screens, and their tendency to be caught in the screens is diminished while their dislodging from the screens is improved.

What is claimed is:

1. The method of determining the relative weight proportions of differently sized fractions of a sample of particulate material, which includes the steps of:
   a. entraining a sample of the material in a moving body of fluid;
   b. depositing a first fraction of the material at one region within the body of fluid to classify such fraction by particle size and depositing a second fraction of the material at a second region within the body of fluid;
   c. measuring the weight increase caused by the deposition of said second fraction at said second region;
   d. entraining said first fraction in said fluid and depositing it at said second region to accumulate thereat with said second fraction; and
   e. measuring the weight increase caused by the deposition of said first fraction at said second region.

2. The method according to claim 1 wherein said section fraction is of smallest particle size and is deposited directly in said second region while said first fraction is being deposited in said first region.

3. The method according to claim 1 including the step of separately introducing further fluid into said body of fluid to create a swirling action therein during step (d).

4. The method of determining the relative weight proportions of differently sized fractions of a sample of particulate material, which comprises the steps of:
   a. entraining the sample of particulate material in a fluid and passing said fluid with entrained material through a succession of sieves having progressively decreasing opening sizes until fractions of said sample are segregated by particle sizes at said sieves;
   b. entraining one of said fractions in said fluid and discharging same to a collection zone;
   c. passing the fluid with the entrained fraction through a porous weighing member at said collection zone to deposit such fraction on said weighing member;
   d. measuring the increase in weight of the weighing member caused by the fraction deposited in step (c);
   e. repeating steps (b) through (d) for at least one other fraction; and
   f. determining the relative weight proportions of the fractions deposited on said weighing member from the measurements effected according to step (d).

5. The method of determining the relative weight proportions of different fractions of a sample of particulate material, which comprises the steps of:
   a. entraining the sample in a moving body of fluid and passing such fluid continuously through a porous weighing member residing in said body of fluid;
   b. separating all but one of said fractions to reside in different regions in said body of fluid before passing through said porous weighing member whereby said one fraction only deposits on said weighing member;
   c. measuring the weight of said one fraction deposited on said weighing member;
   d. re-entraining a further fraction in said body of fluid whereby said further fraction is deposited on said weighing member cumulatively with the previously deposited fraction;
   e. measuring the weight increase caused by the deposition of step (d); and
   f. repeating steps (d) and (e) until all fractions have been cumulatively deposited on said weighing member.

6. The method according to claim 5 including the steps of entraining a second sample in the fluid after the first sample is completely processed and repeating steps (a) through (f) until all fractions of the second sample have been deposited on said weighing member cumulatively with the deposited fractions of the first sample.

7. Apparatus for determining the relative weight proportions of differently sized fractions of a sample of particulate material, comprising in combination:

housing means having an inlet opening at the upper region thereof and a discharge outlet at the lower region thereof;

a plurality of screen members disposed substantially horizontally within said housing and separating the interior of the same into a plurality of stacked compartments or chambers successively leading from the inlet opening to the discharge opening;

means for creating pulsating fluid flow back and forth between said chambers;

means for selectively discharging particulate material retained in said chambers;

conduit means connected to said selected discharge means for directing conveying liquid and particulate material away from the individual chambers;

a closed porous retaining member connected to said means last mentioned whereby sequentially to accumulate particulate materials from the several chambers; and means for weighing the contents of said closed member.

8. Apparatus as defined in claim 7 wherein said means for selectively discharging particulate material comprises a tangential inlet for each of said chambers for selectively discharging fluid thereinto and wherein said conduit means presents a central inlet in each chamber for receiving the particulate material entrained in such fluid.

9. Apparatus as defined in claim 7 wherein said means for selectively discharging particulate material comprises a paddle assembly in each chamber, means for selectively rotating each paddle assembly, and means for selectively introducing fluid into said chamber, said conduit means comprising a discharge pipe for each chamber and having a downturned end portion disposed centrally in a respective chamber, said paddle assembly being mounted for rotation about said downturned end portion and having at least two blades sweeping the region immediately above an associated screen member, each blade being angled to direct particulate material toward said downturned end portion of its associated discharge pipe.

10. The method of determining the relative weight proportions of differently sized fractions of a sample of particulate material, which includes the steps of:

a. entraining said particulate material within a conveying fluid while maintaining a unidirectioned net flow of said fluid to an accumulating chamber;

b. intercepting said fractions and temporarily retaining them in discrete zones within the body of conveying fluid while accumulating one fraction at said accumulating chamber;

c. weighing the accumulated fraction;

d. altering the net direction of conveying fluid flow to convey a second fraction to said accumulating chamber; and e. weighing the accumulated weight of said one and said second fraction.

* * * * *